US010254644B2

(12) United States Patent
Quintanilha et al.

(10) Patent No.: US 10,254,644 B2
(45) Date of Patent: Apr. 9, 2019

(54) METROLOGY METHODS, METROLOGY APPARATUS AND DEVICE MANUFACTURING METHOD

(71) Applicant: ASML Netherlands B.V., Veldhoven (NL)

(72) Inventors: Richard Quintanilha, Eindhoven (NL); Nitish Kumar, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/614,551

(22) Filed: Jun. 5, 2017

(65) Prior Publication Data

US 2017/0357155 A1 Dec. 14, 2017

(30) Foreign Application Priority Data

Jun. 9, 2016 (EP) ..................... 16173755

(51) Int. Cl.
*G03B 27/54* (2006.01)
*G03F 7/00* (2006.01)
(Continued)

(52) U.S. Cl.
CPC .......... *G03F 7/0002* (2013.01); *G03F 7/0005* (2013.01); *G03F 7/2004* (2013.01);
(Continued)

(58) Field of Classification Search
CPC .... G03F 7/0002; G03F 7/0005; G03F 7/2004; G03F 7/2008; G03F 7/70625; G03F 7/70633; G03F 9/7019; G01N 21/956
See application file for complete search history.

(56) References Cited

U.S. PATENT DOCUMENTS

2005/0254050 A1   11/2005   Fielden et al.
2006/0285120 A1   12/2006   Aiyer
(Continued)

FOREIGN PATENT DOCUMENTS

WO   WO 2016/150957 A1   9/2016
WO   WO 2017/108404 A1   6/2017

OTHER PUBLICATIONS

International Search Report and Written Opinion directed to International Patent Application No. PCT/EP2017/061670; 11 pages.
(Continued)

*Primary Examiner* — Peter B Kim
(74) *Attorney, Agent, or Firm* — Sterne, Kessler, Goldstein & Fox P.L.L.C.

(57) ABSTRACT

A metrology apparatus uses radiation (304) in an EUV waveband. A first detection system (333) includes a spectroscopic grating (312) and a detector (313) for capturing a spectrum of the EUV radiation after interaction with a target (T). Properties of the target are measured by analyzing the spectrum. The radiation (304) further includes radiation in other wavebands such as VUV, DUV, UV, visible and IR. A second detection system (352, 372, 382) is arranged to receive at least a portion of radiation (350) reflected by the first spectroscopic grating and to capture a spectrum (SA) in one or more of said other wavebands. The second waveband spectrum can be used to enhance accuracy of the measurement based on the EUV spectrum, and/or it can be used for a different measurement. Other types of detection, such as polarization can be used instead or in addition to spectroscopic gratings.

18 Claims, 8 Drawing Sheets

(51) Int. Cl.
*G03F 7/20* (2006.01)
*G01N 21/956* (2006.01)
*G03F 9/00* (2006.01)

(52) U.S. Cl.
CPC ........ *G03F 7/2008* (2013.01); *G03F 7/70625* (2013.01); *G03F 7/70633* (2013.01); *G01N 21/956* (2013.01); *G03F 9/7019* (2013.01)

(56) References Cited

U.S. PATENT DOCUMENTS

| | | |
|---|---|---|
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2012/0123748 A1 | 5/2012 | Aben et al. |
| 2013/0215404 A1 | 8/2013 | Den Boef |
| 2013/0258310 A1 | 10/2013 | Smilde et al. |
| 2013/0271740 A1 | 10/2013 | Quintanilha |
| 2015/0138523 A1 | 5/2015 | Jak et al. |

OTHER PUBLICATIONS

Danylyuk et al., "Multi-angle spectroscopic extreme ultraviolet reflectometry for analysis of thin films and interfaces," Phys. Status Solidi C, vol. 12, No. 3, 2015; pp. 318-322.

METROLOGY METHODS, METROLOGY APPARATUS AND DEVICE MANUFACTURING METHOD

BACKGROUND

Field of the Invention

The present invention relates to methods and apparatus for metrology usable, for example, in the manufacture of devices by lithographic techniques and to methods of manufacturing devices using lithographic techniques. Methods of measuring critical dimension (line width) are described, as a particular application of such metrology. Methods of measuring asymmetry-related parameters such as overlay are also described.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer).

In lithographic processes, it is desirable frequently to make measurements of the structures created, e.g., for process control and verification. Various tools for making such measurements are known, including scanning electron microscopes (SEM), which are often used to measure critical dimension (CD). Other specialized tools are used to measure parameters related to asymmetry. One of these parameters is overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis. Compared with SEM techniques, optical scatterometers can be used with much higher throughput, on a large proportion or even all of the product units.

The targets used by conventional scatterometers are relatively large, e.g., 40 µm by 40 µm, gratings and the measurement beam generates a spot that is smaller than the grating (i.e., the grating is underfilled). In order to reduce the size of the targets, e.g., to 10 µm by 10 µm or less, e.g., so they can be positioned in amongst product features, rather than in the scribe lane, so-called "small target" metrology has been proposed, in which the grating is made smaller than the measurement spot (i.e., the grating is overfilled). These targets can be smaller than the illumination spot and may be surrounded by product structures on a wafer. Typically small targets are used for measurement of overlay and other performance parameters that can be derived from measurements of asymmetry in the grating structure. By placing the target in among the product features ("in-die target"), it is hoped to increase accuracy of measurement. The improved accuracy is expected for example because the in-die target is affected by process variations in a more similar way to the product features, and less interpolation may be needed to determine the effect of a process variation at the actual feature site. These optical measurements of overlay targets have been very successful in improving overlay performance in mass production. So-called dark-field imaging has been used for this purpose. Examples of dark field imaging metrology can be found in international patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20130258310A, US20130271740A and US2015138523. Similar small target techniques for focus performance and dose performance have been implemented also. The content of all these prior application is incorporated herein by reference.

As technology develops, however, performance specifications become ever tighter. Moreover, small target techniques have not been developed for measurement of other parameters such as line width or critical dimension (CD). A further limitation of current methods is that they are made with optical wavelengths, much greater than the typical dimensions of real product features. A particular parameter of interest is linewidth (CD). CD metrology suffers from low accuracy, cross-talk between parameters of interest and also between parameters of interest and other hidden parameters (process robustness). As the microscopic structures shrink and become more and more complex in geometry (going to 3-D structures, for example), known techniques of CD metrology struggle to provide accuracy, precision, and speed. Another parameter of interest is overlay.

An attractive option for improving the measurement of smaller features is to use radiation with wavelengths shorter than the wavelengths used in the conventional scatterometers. Radiation can be used in wavebands such as those known as ultraviolet (UV), deep ultraviolet (DUV) radiation, vacuum UV (VUV), extreme UV (EUV), soft x-ray (SXR) and x-ray. These wavebands are of course simply named regions of a continuous electromagnetic spectrum, rather than having any hard physical definition. The bands can be defined differently by different workers, and may overlap one another.

Reflectometry techniques using X-rays (GI-XRS) and extreme ultraviolet (EUV) radiation at grazing incidence are known for measuring properties of films and stacks of layers on a substrate. Within the general field of reflectometry, goniometric and/or spectroscopic techniques can be applied. In goniometry, the variation of a reflected beam with different incidence angles is measured. Spectroscopic reflectometry, on the other hand, measures the spectrum of wavelengths reflected at a given angle (using broadband radiation). For example, EUV reflectometry has been used for inspection of mask blanks, prior to manufacture of reticles (patterning devices) for use in EUV lithography. Work on these techniques has been described for example by S Danylyuk et al in "Multi-angle spectroscopic EUV reflectometry for analysis of thin films and interfaces", Phys. Status Solidi C 12, 3, pp.318-322 (2015). However, such measurements are different from the measurement of CD in a periodic structure. Moreover, particularly in view of the very shallow grazing incidence angles involved, none of these known techniques is suitable for metrology on small targets such as an in-die grating.

In pending international patent application PCT/EP2016/056254, not published at the present priority date, it is proposed to measure properties such as CD and overlay of target structures using EUV radiation, that is radiation in the wavelength range from about 1 nm to about 100 nm. Spectroscopic reflectometry is performed using radiation scattered at zero and/or higher diffraction orders. A smaller spot size is achieved than in T-SAXS or GI-SAXS methods, using a higher grazing angle of incidence than can be used at x-ray wavelengths. Diffraction signals are further strengthened by the use of a conical mount between an EUV optical system and the substrate. This allows a non-zero azimuthal angle of incidence relative to a direction of periodicity of the target structure. The contents of the prior application are hereby incorporated by reference in the present disclosure.

Such techniques using radiation in the extreme ultraviolet (EUV) waveband offer particular advantages for metrology of CD, overlay and other properties of small metrology targets. Conveniently these small metrology targets may again have the form of periodic structures. Compared with the optical scatterometry commonly practiced, EUV rays will not be strongly influenced by underlying features, and modeling of the periodic structure itself can be more accurate as a result. In order to obtain sufficient information for CD metrology, spectral properties across a range of EUV wavelengths can be measured. On the other hand, making measurements of a target structure using radiation in different wavelength ranges and/or using different properties of the radiation can be beneficial. For example, when measurements using radiation in different wavebands are combined in a reconstruction or similar method, accuracy in the calculated measurements of a property of interest can be improved. When using radiation in a single waveband, cross-correlation between different properties of the material and/or geometry of the structure can lead to error and/or uncertainty in a calculated property of interest. Using information from additional wavebands, some of these errors and uncertainties can be resolved. Of course, measurements in different wavelength ranges can also be used independently to measure two different properties.

In the mentioned international patent application, a form of hybrid metrology is proposed in which larger targets with product-like structures are measured using the EUV radiation, while smaller in-die targets are measured using an angle-resolved scatterometer working in a more conventional optical waveband. The results of the EUV measurements on a few substrates are used to calibrate the optical measurements in high-volume manufacture. In a European patent application 15202273.7, also not published at the present priority date, metrology apparatus based on EUV spectroscopic reflectometry and an angle-resolved scatterometer working in (for example) the optical waveband are combined in a single apparatus. The contents of the European patent application are incorporated herein by reference. Although in these prior applications the apparatus required for making measurements at different wavelength ranges is housed together and shares certain common infrastructure, the different measurements are nevertheless are made using separate sources and optical systems within the same apparatus.

SUMMARY OF THE INVENTION

The invention aims to provide alternative methods and apparatus for metrology for determining properties of microscopic structures of the type found in semiconductor manufacturing or elsewhere.

The invention in a first aspect provides a metrology apparatus for measuring a property of a structure, the metrology apparatus comprising:

an illumination system for irradiating the structure with radiation;

a first detection system comprising a first spectroscopic grating and a first detector, the first spectroscopic grating being arranged to receive said radiation after interaction with the structure, the first detector being arranged to detect a spectrum in a first waveband by receiving one or more higher orders of radiation diffracted by said first spectroscopic grating;

a second detection system arranged to receive at least a portion of zero order radiation reflected by the first spectroscopic grating and to analyze said zero order radiation in one or more other wavebands.

The inventors have recognized that measurements in one or more additional wavebands can be made, by exploiting the broadband nature of an EUV radiation source, without the need for separate illumination and separate metrology timing. In particular, the inventors have recognized that a spectroscopic grating which is used to analyze the spectrum of radiation in the first waveband, may as a by-product deliver radiation that contains further information about the target structure in one or more different wavebands. For example, a spectroscopic grating may be used to obtain a spectrum of radiation in an EUV waveband. At the same time, zero order reflected radiation from the grating may contain information about the structure and longer wavelength wavebands, for example VUV, DUV, EUV and visible wavebands. In embodiments using a broadband source, spectral information for different wavebands information can be obtained simultaneously, without adding to the measurement time. The increase in the apparatus cost may also be very modest.

Reference to a range of wavelengths from 1 nm to 100 nm is not intended to mean that the apparatus or method should use wavelengths across that entire wave range, or even be capable of doing so. An individual implementation may choose to work with wavelengths over only a subset of the range. The appropriate range will depend on the availability of suitable sources, and the dimension of structures to be measured.

In a particular implementation, the metrology system includes a substrate support adapted to receive semiconductor wafers (for example 300 mm wafers) from an automated wafer handler.

In a second aspect of the invention, there is provided a method of measuring a property of a structure manufactured by a lithographic process, the method comprising the steps:

(a) irradiating the structure with radiation including radiation in a first waveband and radiation in a second waveband;

(b) directing at least a portion of said radiation after interaction with the structure to a first spectroscopic grating;

(c) detecting a spectrum in a first waveband using one or more higher orders of radiation diffracted by said first spectroscopic grating;

(d) analyzing at least a portion of zero order radiation reflected by the first spectroscopic grating in the second waveband.

The invention further provides a device manufacturing method comprising:

transferring a pattern from a patterning device onto a substrate using a lithographic process, the pattern defining at least one structure;

measuring one or more properties of the structure to determine a value for one or more parameters of the lithographic process; and applying a correction in subsequent operations of the lithographic process in accordance with the measured property, wherein the step of measuring the properties of the structure includes measuring a property using the metrology apparatus according to the first aspect of the invention as set forth above.

The invention further provides a device manufacturing method comprising:

transferring a pattern from a patterning device onto a substrate using a lithographic process, the pattern defining at least one structure;

measuring one or more properties of the structure to determine a value for one or more parameters of the lithographic process; and applying a correction in subsequent operations of the lithographic process in accordance with the measured property, wherein the step of measuring the properties of the structure includes measuring a property using the method according to the second aspect of the invention as set forth above.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example, with reference to the accompanying drawings in which.

DETAILED DESCRIPTION OF EXEMPLARY EMBODIMENTS

Before describing embodiments of the invention in detail, it is instructive to present an example environment in which embodiments of the present invention may be implemented.

Figure 1:
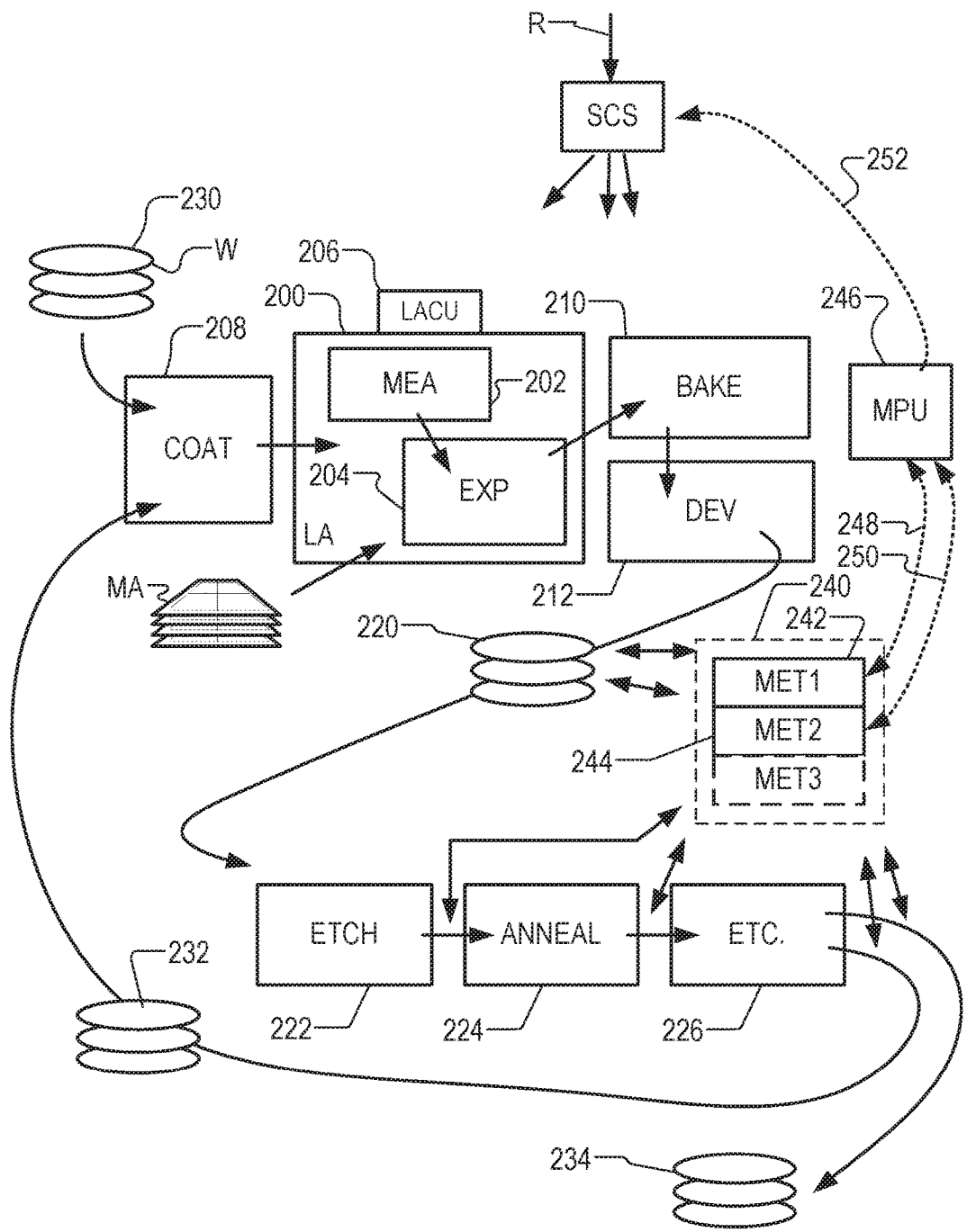
FIG. 1 depicts a lithographic apparatus together with other apparatuses forming a production facility for semiconductor devices, and including a metrology apparatus according to an embodiment of the present invention.

FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of ma4ny marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes a metrology system 240 which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Using metrology system 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, hybrid metrology system 240 and/or other metrology apparatuses (not shown) can be applied to measure properties of the processed substrates 232, 234, and incoming substrates 230.

Each generation of lithographic manufacturing technology (commonly referred to as a technology "node") has tighter specifications for performance parameters such as CD. One of the main challenges in metrology is that the metrology target size is desired to be smaller than the targets customarily used with metrology apparatus 240. For example, a present goal is to use targets with a size of 5 µm×5 µm or smaller. These small sizes would permit wider use of so-called "in-die" or "on product" metrology, where targets are located among the product features (instead of being confined in scribe lane areas between product areas).

Within metrology system 240, a first metrology apparatus 242 (MET1) and second metrology apparatus 244 (MET2) and optionally further apparatuses (MET3 etc.) are provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. By providing multiple metrology apparatuses 242, 244 etc., multiple types of measurement can be performed to obtain a better overall measurement of a parameter or parameters of interest on a given target structure, or of course to obtain separate measurements of different parameters of interest. The metrology apparatuses 242, 244 etc. may be provided as separate units, into which substrates are loaded and unloaded and unloaded for each type of measurement alternatively, two or more of these metrology apparatuses may be integrated into a hybrid metrology apparatus, so that they may work on a common substrate. Examples of such hybrid metrology apparatus are disclosed in the above-mentioned European patent application 15202273.7, the contents of which are incorporated herein by reference.

Each of the metrology apparatuses 242, 244 can have a particular illumination system for radiation of a particular characteristic. More detailed examples of the types of apparatuses that can be combined will be given below. In each case, metrology processing system 246 receives first spectrum data 248 from a first detection system within the first metrology apparatus 242 and receives second spectrum data 250 from a second detection system within the second metrology apparatus 244. Metrology processing system 246 combines these spectra in a hybrid calculation obtain the measurements 252 of CD or other parameters that are reported to the supervisory control system SCS. In some embodiments, metrology processing system 246 also controls operation of one or more of the metrology apparatuses 242, 244 to vary parameters of its operation, based on to spectrum data received from the other one of the metrology apparatuses.

One of the metrology apparatuses, for example the second metrology apparatus 244, may be designed to operate with radiation at visible or UV wavelengths, while another of the apparatuses, for example the first metrology apparatus 242 may be designed to operate with EUV radiation. In other embodiments, both the first and second metrology apparatuses may be designed to operate with EUV radiation, of the same or different wavelengths. One of the apparatuses may be designed to operate with grazing incidence while another is designed to operate with normal or near-normal incidence. One of the apparatuses may be designed to obtain a frequency-resolved spectrum of radiation scattered by the target structure, while another of the apparatuses is designed to obtain an angle-resolved spectrum. One of the metrology apparatuses, for example the second metrology apparatus 244 may be an angle-resolved scatterometer, a spectroscopic scatterometer, a spectroscopic ellipsometer, and/or a spectroscopic Mueller ellipsometer. These and other variants can be used in the hybrid system to obtain more information about a structure, and so give more accurate measurements of a parameter of interest. Three or more metrology apparatuses can be provided within metrology system 240, and the first and second metrology apparatuses are labeled here only for convenience. These additional metrology apparatuses can be used all together in making one measurement, or they may be used in different sub-combinations. In the example of the hybrid metrology system mentioned above, some common hardware can be used to implement more than one of these types of metrology apparatus.

In embodiments of the hybrid metrology system 240 according to the present disclosure, it is proposed to use EUV wavelengths for metrology in at least one of the metrology apparatuses. In some embodiments, EUV reflectometry, in particular spectroscopic EUV reflectometry, is employed as part of the CD-metrology solution for future technological nodes. In the pending international patent application PCT/EP2016/056254, mentioned above, it is demonstrated that EUV reflectometry offers benefits of high sensitivity, being robust against process variations and being selective for a parameter of interest.

Like the optical scatterometer used in today's production facilities, EUV metrology apparatus can be used to measure structures within the resist material treated within the litho cell (called "after develop inspection" or ADI), and/or to measure structures after they have been formed in harder material (called "after etch inspection" or AEI). For example, substrates may be inspected using EUV metrology apparatus 242 after they have been processed by the developing apparatus 212, etching apparatus 222, annealing apparatus 224 and/or other apparatus 226. By contrast, X-ray techniques will generally be limited to AEI and cannot be used to measure structures formed only in the resist. This restricts the possibility to re-work substrates if they fail an inspection.

EUV Spectroscopic Reflectometry

Figure 2:
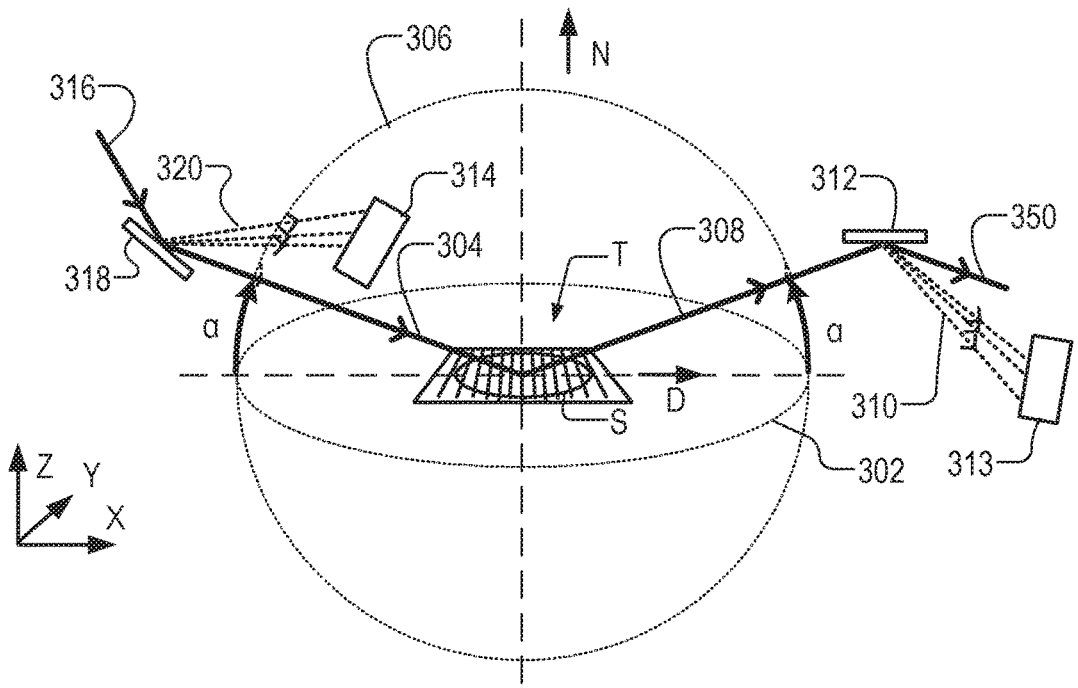
FIG. 2 illustrates the geometry of incident and reflected rays in relation to a grating target and a first detection system for performing EUV spectroscopic reflectometry in one embodiment of the metrology apparatus of FIG. 1.
Figure 3:
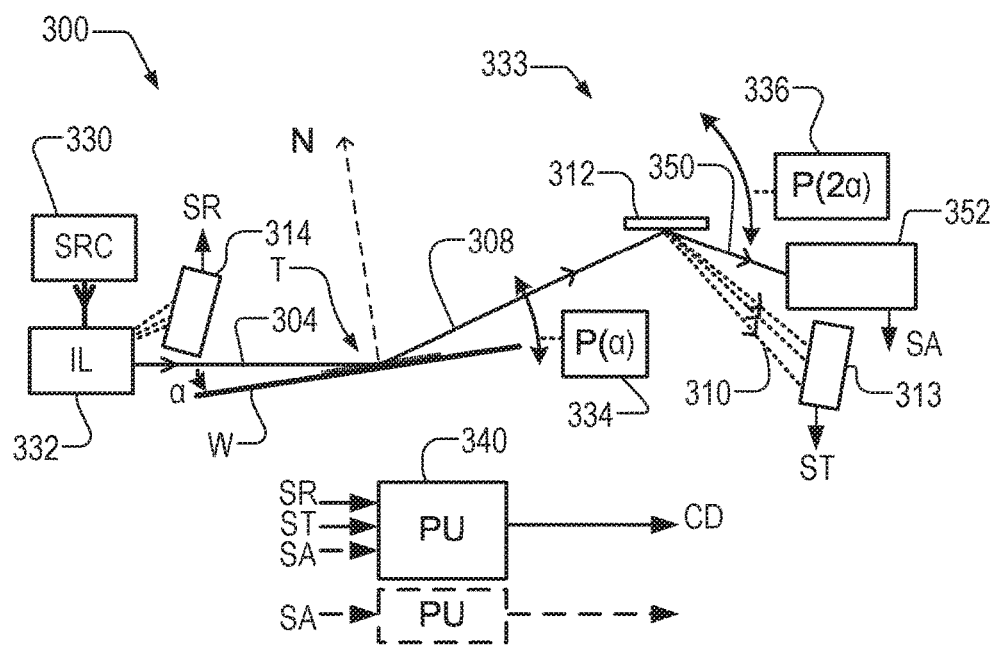
FIG. 3 illustrates schematically the components of the metrology apparatus, performing the EUV metrology method of FIG. 2, and showing the addition of a second detection system.

FIG. 2 illustrates an EUV metrology method while FIG. 3 illustrates an EUV metrology apparatus 300. The apparatus can be used as an example of the first metrology apparatus 242 or second metrology apparatus 244 for measuring parameters of substrates W processed in the production facility of FIG. 1.

In FIG. 2, the target T is represented schematically as comprising a one-dimensional grating structure at the origin of a spherical reference frame. Axes X, Y and Z are defined relative to the target. (Of course any arbitrary coordinate system can be defined in principle, and each component may have its own local reference frame, that can be defined relative to the one shown.) The direction of periodicity D of the target structure is aligned with the X axis. This one-dimensional grating structure takes the shape of a periodic series of lines in a grating, but is only one example of many possible target structures. Other examples include features in a 2-D array, like contact holes or pillars in a device pattern. In other cases, the target structure may be a multi-layer structure with no variation in X or Y.

The drawing is not a true perspective drawing, but a schematic illustration only. The X-Y plane is the plane of the target and substrate, and for clarity is shown tilted toward the viewer, represented by an oblique view of circle 302. The Z direction defines the direction N normal to the substrate. In FIG. 2, one of the incident rays is labeled 304 and has an angle α of grazing incidence. In this example, the incident ray 304 (and all incident rays forming the radiation spot S) lie substantially in a plane parallel to the X-Z plane, that is a plane defined by the directions D and N and represented by circle 306. A reflected ray 308 that is not scattered by the periodic structure of the target T emerges towards the right hand side of the target in the diagram, with an elevation angle α.

To perform spectroscopic reflectometry, ray 308 and other reflected rays are broken into a spectrum 310, comprising rays of different wavelengths. The spectrum may be produced for example using a grazing incidence diffraction grating 312. The spectrum 310 comprises one or more higher orders of radiation diffracted by the grating 312, is detected by a detector 313. This detector, which may for example be a CCD image detector having an array of pixels, is used to transform the spectrum into electrical signals and eventually digital data for analysis.

In a practical system, the spectrum of illumination radiation (that is, the radiation including the incident ray 304) may be subject to time variations, which would disturb the subsequent analysis. In order to normalize the detected spectrum against these variations, a reference spectrum is captured by a second detector 314. To produce the reference spectrum, source radiation 316 is diffracted by another diffraction grating 318. A zero order reflected ray of grating 318 forms the incident ray 304, while the first order diffracted rays 320 of grating 318 form the reference spectrum detected by reference spectrum detector 314. Electrical signals and data representing the reference spectrum are obtained for use in the analysis.

From the measured spectrum, obtained for one or more values of incidence angle α, a measurement of a property of the target structure T can be calculated. In the metrology system 240, this measurement may be obtained by using the detected spectrum in combination with one or more spectra detected by other metrology apparatuses on the same target structure. Different ways of making this combination are described further in the above-mentioned European patent application 15202273.7.

Turning to FIG. 3, an EUV metrology apparatus 300 is provided for measuring properties of a metrology target T formed on substrate W, by the method of FIG. 2. Various hardware components are represented schematically. The practical implementation of these components can be performed by the relevant skilled persons applying a mixture of existing components and specially-designed components, according to well-known design principles. A support (not shown in detail) is provided for holding the substrate at a desired position and orientation relative to other components to be described. A radiation source 330 provides radiation to an illumination system 332. Illumination system 332 provides a beam of EUV radiation represented by ray 304 which forms a focused irradiation spot on target T. Illumination system 332 also provides the reference spectrum 320 to detector 314. Components 312, 313 etc. may be conveniently considered as a detection system 333.

Substrate W in this example is mounted on a movable support having a positioning system 334 such that an angle of incidence a of ray 304 can be adjusted. In this example, it is chosen as a matter of convenience to tilt the substrate W to change the incidence angle, while the source 330 and illumination system 332 remain stationary. In order to catch the reflected ray 308, detection system 333 is provided with a further movable support 336, so that it moves through an angle 2 α relative to the stationary illumination system, or through an angle a relative to the substrate. In the grazing incidence regime of EUV reflectometry, it is convenient to define the incidence angle α by reference to the plane of the substrate, as shown. Of course, it could equally be defined as an angle between the direction of incidence of incident ray I and a direction N normal to the substrate.

Additional actuators, not shown, are provided for bringing each target T into a position where the focused spot S of radiation is located. (Looking at it another way, to bring the spot to the position where the target is located.) In a practical application, there may be a succession of individual targets or target locations to be measured on a single substrate, and a succession of substrates too. It is immaterial, in principle, whether the substrate and target are moved and reoriented while the illumination system and detector stay still, or whether the substrate stays still while the illumination system and detector are moved, or whether different components of the relative movement are achieved by a combination of these techniques. The present disclosure encompasses all these variants.

As already described with reference to FIG. 2, the radiation reflected by target T and substrate W is split into a spectrum 310 of rays of different wavelengths by a grating 312, before it impinges on detector 313. Detector 306 comprises for example a position-sensitive EUV detector, typically an array of detector elements. The array may be a linear array, but in practice a 2-dimensional array of elements (pixels) may be provided. Detector 313 may be for example a CCD (charge coupled device) image sensor.

A processor 340, which may be part of the metrology processing system 246 or a sub-system local to the metrology apparatus 300, receives signals from the detectors 313 and 314. In particular, signal ST from detector 313 represents the target spectrum and signal SR from detector 314 represents the reference spectrum. Processor 340 can subtract the reference spectrum from the target spectrum to contain a reflection spectrum of the target, normalized against variation in the source spectrum. The resulting reflection spectra for one or more angles of incidence are used in the processor 340 to calculate indirectly a measurement of property of the target, for example CD or overlay.

In practice, radiation from source 330 may be provided in a series of short pulses and signals SR and ST may be captured together for each pulse. Difference signals for each individual pulse are calculated, before being aggregated into an overall reflection spectrum for this target at this angle of incidence. In this way, instability of the source spectrum between pulses is corrected for. The pulse rate may be thousands, or even tens of thousands per second (hertz). The number of pulses aggregated to measure one reflection spectrum may be tens, hundreds, or thousands, for example. Even with so many pulses, the physical measurement takes a fraction of one second.

First and Second Detection Systems

The grating 312 and detector 313 may together be regarded as a first detection system 333 in the apparatus of FIG. 3. The first detection system 333 may further include the grating 318 and detector 314 which produce the reference spectrum signal SR. The EUV radiation included in spectrum 310 may be regarded as radiation in a first waveband. Radiation which is not diffracted to form spectrum 310 on detector 313 forms a beam of zero order radiation 350, as illustrated in FIGS. 2 and 3. Where the illuminating radiation from the source 330 and illumination system 332 includes ranges of wavelengths much longer than the EUV radiation diffracted by grating 312, these will be effectively included in the zero order radiation 350. This is because the grating pitch of the grating 312 is tuned to the much shorter wavelengths in the first waveband, and is much too short to be "seen" by the longer wavelengths of the second waveband. In accordance with principles of the present disclosure, a second detection system 352 and/or further detection systems are arranged to receive this zero order radiation, and to perform further analysis in a second waveband and/or further wavebands.

Second detection system 352 provides one or more additional signals SA, as will be described in more detail later. In an example where source 330 and illumination system 332 can deliver broadband radiation that includes radiation in first and second wavebands simultaneously, the additional signals SA can be obtained simultaneously with the signals ST and SR, without necessarily incurring any additional exposure time or adjustment. Even in a case where radiation in the first and second wavebands is generated sequentially, rather than simultaneously, the radiation 350 reflected by the first spectroscopic grating 312 provides a convenient source of information, avoiding the need for additional optical systems in the vicinity of the target T.

The additional signals SA from the second and/or further detection systems 352 may be used by processor 340 enhance the measurement accuracy of the measurements calculated from the EUV spectrum signal ST. Using only a single waveband of radiation, the accuracy reached is limited by the cross-correlation between the optical properties of the material and the geometrical properties of the target structure (multilayer and/or gratings). By increasing the diversity in the data, particularly in terms of wavelength the accuracy of measurements of parameters such as CD and overlay can be improved. Alternatively or in addition, as shown in broken lines, the additional signal SA be used by processor 340 or in the processor for a completely separate measurement purpose.

Figure 10:
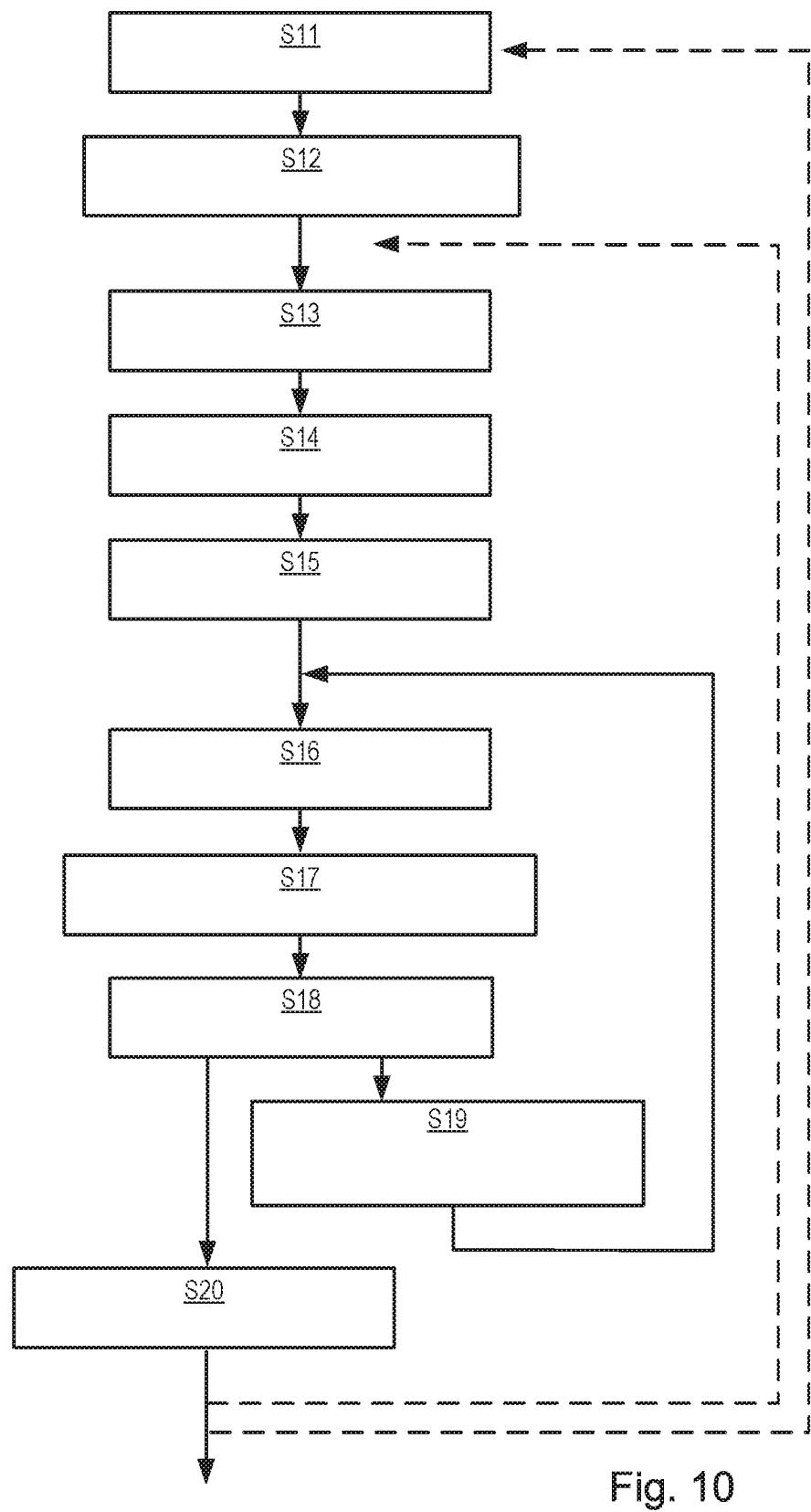
FIG. 10 is a flow chart illustrating a metrology method according to an embodiment of the present invention.

In the example illustrated, the first waveband includes EUV radiation, and the first detection system is an EUV spectroscopic reflectometer, including the spectroscopic grating 312. In the application of this EUV-SR to metrology in semiconductor manufacturing, small grating targets can be used. These may for example have dimensions smaller than 10 μm in each direction X and Y. Multiple diffraction spectra are captured using detectors 313 and 314, while setting the grazing angle of incidence a to various different values. Using the detected spectra and a mathematical model of the target structure, reconstruction calculations can be performed to arrive at measurement of CD and/or other parameters of interest. An example reconstruction method is illustrated in FIG. 10, described below. In the metrology system that is the subject of the present disclosure, the reconstruction method can be modified to take account of spectra or other analytical information detected by two or more detection systems operating in different wavebands, and not only the spectrum in the first waveband, represented by signal ST.

Considering briefly the target itself, dimensions of the lines and spaces will depend on the target design, but the period of the structure may be for example less than 100 nm, less than 50 nm, less than 20 nm, even less than 10 nm and down to 5 nm. The lines of the grating structure may be of the same dimension and pitch as product features in a product area of the substrate. The lines of the grating structure may in fact be the lines of a product structure, rather than a target structure formed, within a dedicated target area, solely for the purposes of metrology. Such small features may be formed for example in an EUV lithography process, by imprint lithography or by direct-write methods. Such small features may also be formed using present-day DUV lithography, by a so-called double-patterning processes (generally multiple-patterning). Techniques in this category include pitch-doubling, for example by litho-etch-litho-etch (LELE) and self-aligned dual-damascene in back end-of the line (BEOL) layers. For the purposes of explanation, it will be assumed in the following examples that CD is the parameter of interest. However, where there are two gratings formed on top of one another, another parameter of interest may be overlay. This can be measured based on asymmetry in the EUV-SR diffraction orders. Any unintentional positional offset between different populations of features in a multiple-patterning process can be regarded as a form of overlay, and can be measured by analogous techniques to those used to measure overlay between layers. Additionally, overlay against features in an underlying or overlying layer can be different for each population when multiple populations of features are formed in a single layer, and overlay for each of these populations can be measured separately if desired. Techniques for measuring these types of overlay are described further in the above-mentioned European patent application 15202273.7. The incidence angle can be elevated if necessary to achieve adequate penetration of the EUV radiation to the lower structure.

Figure 4:
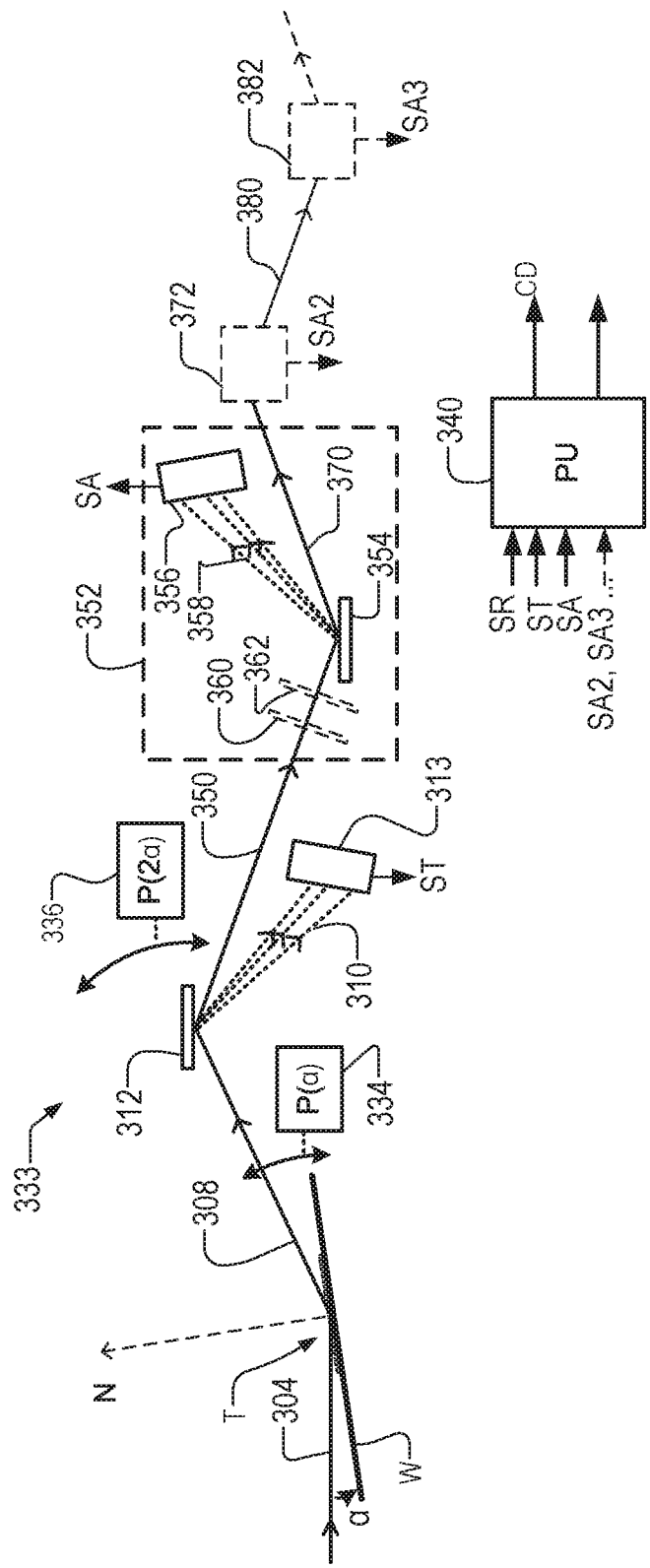
FIG. 4 illustrates schematically part of the apparatus of FIG. 3, including more detail of one example of a second detection system and including optionally third and fourth detection systems.

FIG. 4 illustrates in more detail an example of the second detection system 352 that may be arranged to receive the zero order reflected radiation 350 in an apparatus of FIG. 3. In this example, an additional signal SA represents a spectrum of the radiation reflected by the target T in a second waveband, which is assumed to contain wavelengths longer than the EUV radiation is spectrum 310 is detected by detector 313. Second detection system 352 has a very similar form to the first detection system, comprises a second spectroscopic grating 354 and a second detector 356. Second spectroscopic grating 354 diffracts a portion of radiation in a second waveband to form a second spectrum 358, which is detected by second detector 356. Additional signal is a represents this second spectrum.

Second detection system 352 may include additional components, such as a wavelength-selecting filter 360 and an analyzer 362 for selecting a particular polarization of radiation, but these are purely optional.

In the case where second detection system 352 includes a spectroscopic grating 354, this grating also outputs zero order reflected radiation 370, as well as the second spectrum 358. In the same way as the zero order radiation 350 from the first spectroscopic grating 312 can be used in the second detection system, so the zero order radiation 370 from the second spectroscopic grating 354 can be delivered to a third detection system 372. Further additional signals SA2 can be generated by this third detection system, and used, either alone or in combination with the other signals already received by processor 340, to improve measurement accuracy, and/or to allow different measurements to be made. Additionally, within the third detection system 372, there may be a spectroscopic grating that delivers zero order reflected radiation 382 to a fourth detection system 382, and so on. Further additional signals SA3 can be generated by this fourth detection system and used, either alone or in combination with the other signals already received by processor 340, to improve measurement accuracy and/or to allow different measurements to be made.

The choice of the different wavebands as a matter of design choice and practicality. Purely for the sake of example, it is assumed in the present examples that the first waveband comprises EUV radiation, for example including wavelengths in some or all of the range 1 nm to 100 nm. Each further waveband, such as the second waveband, third waveband and so on can for example be longer than the first waveband. The second waveband may, for example, include a longer-wavelength portion of the EUV waveband, or it may comprise wavelengths longer than 100 nm. For example, the second waveband may comprise wavelengths in the range 100 to 300 nm, including so-called vacuum UV and/or deep UV radiation. Alternatively, the second waveband may comprise wavelengths longer than 300 nm, for example in the UV and/or visible and/or infrared wavelengths. Similarly, where radiation is analyzed in a third waveband, wavelengths in this third waveband may be longer than those in the second waveband, and may comprise, for example, ultraviolet, visible and/or infrared wavelengths.

In principle, the sequence of wavebands over the first, second, third etc. detection systems need not be ever-increasing in wavelength, but in practical systems, this is likely to be the most convenient arrangement. One reason for this is that, where a detection system includes a spectroscopic diffraction grating, the grating lines that are formed to diffract radiation in one waveband will generally be invisible to radiation and much longer wavebands, so that those longer wavebands can be found in the zero order reflected radiation of the spectroscopic grating. Furthermore, radiation sources generating broadband radiation across several wavebands often generate a greater number of photons in the longer wavelengths than in the short wavelengths. As a result, photons in a short wavelength waveband, such as the EUV waveband, tend to be more "precious" than the longer wavelengths, such as ultraviolet, visible and infrared. Since some portion of these photons will be lost at each optical element, it is desirable to process the less abundant photons, for example the EUV and/or VUV photons, as close as possible to the target, in the overall optical path. One can tolerate some loss of the more abundant, longer wavelength photons, before they are detected in a downstream part of the overall optical system. Additionally, optical systems processing photons at the shortest wavelengths, such as EUV and VUV, may need to be housed in special environments, such as a low pressure (near vacuum) atmosphere. By positioning the detection systems for these shorter wavelengths upstream of the detection systems for longer wavelengths, the detection systems for longer wavelengths can be housed outside the special environment, reducing substantially the cost and size of the apparatus.

In the example of FIG. 4, it is assumed that each of the second, third and fourth detection systems is a spectroscopic detection system, comprising a spectroscopic grating the detector. If necessary, reference signals in one or more of the other wavebands can be included in the reference signal SR or an additional reference signal. In some cases, the source may be well characterized so that by measuring the fluctuation of the first (EUV) waveband, the processor 340 can deduce a reference spectrum for another waveband. If necessary, however, an additional grating and detector (not shown) added upstream of the target structure. Care can be taken so that this grating does not induce undue loss of the EUV radiation.

However, spectroscopy is just one example of the type of analysis that can be made in each waveband. The present disclosure is not limited to spectroscopy as the only form of analysis in each detection system.

Figure 5:
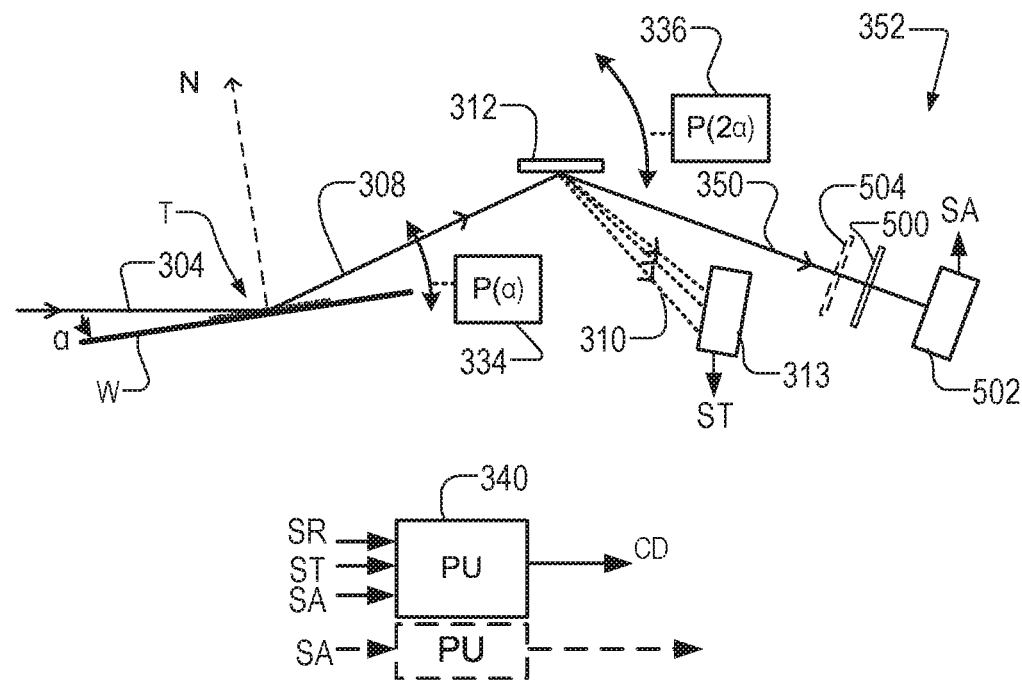
FIG. 5 illustrates schematically part of the apparatus of FIG. 3, including more detail of an alternative example of a second detection.

FIG. 5 illustrates, for example, an alternative form of second detection system 352, in which the second detection system is designed for ellipsometry. A polarization analyzer 500 receives the zero order radiation 350 from the spectra graphic grating 312 the first detection system, and filters out predetermined polarizations of this radiation. A wavelength-selective filter 504 and/or other filter elements may also be provided. The filtered radiation is detected by detector 502, to generate an additional signal SA for use by processor 340. As before, the additional signal SA can be used in combination with the signals SR and ST from the first detection system to enhance accuracy of calculated measurements of CD, overlay and other parameters. Alternatively, or in addition, the additional measurement essay can be used for a separate calculation. A single value of radiation intensity from detector 502 is not likely to yield a lot of information. However, combined with variation of the angle of incidence α, more informative data can be obtained.

Figure 6:
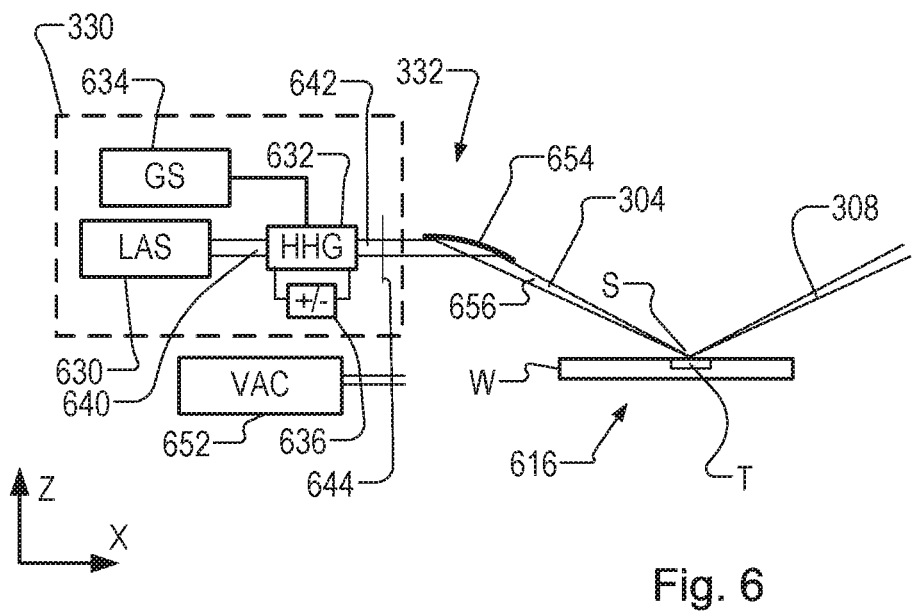
FIG. 6 illustrates schematically the components of a broadband illumination system in one embodiment of the metrology apparatus of FIG. 3.

FIG. 6 illustrates a particular form of radiation source 330 that may be used in the apparatus of FIGS. 3 to 5. Any type of radiation source can be used, provided that it provides an adequate quality of radiation in the desired wavebands. In principle, radiation in the first waveband, second waveband etc. could be provided sequentially, but the maximum throughput of the apparatus will be obtained if radiation in the different wavebands is present simultaneously in the illuminating radiation. This radiation could be combined from different individual sources, or it can be obtained from a single, broadband source of the type illustrated in FIG. 6. Types of radiation source that may be considered include inverse Compton sources (ICS), compact synchrotron sources, laser produced plasma sources (LPP), electrical discharge produced plasma sources (DPP) and higher harmonic generator sources (HHG).

Radiation source 330 in the example of FIG. 6 is an HHG source for generating EUV radiation based on high harmonic generation (HHG) techniques. Such sources are available for example from KMLabs, Boulder Colo., USA (http://www.kmlabs.com/). Main components of the radiation source are a pump laser 630 and an HHG gas cell 632. A gas supply 634 supplies suitable gas to the gas cell, where it is optionally ionized by an electric source 636. The pump laser may be for example a fiber-based laser with an optical amplifier, producing pulses of infrared radiation lasting less than 1 ns (1 nanosecond) per pulse, with a pulse repetition rate up to several megahertz, as required. The wavelength may be for example in the region of 1 μm (1 micron). The laser pulses are delivered as a first radiation beam 640 to the HHG gas cell 632, where a portion of the radiation is converted to higher frequencies. From the HHG gas cell 632 emerges a beam 642 including coherent radiation of the desired wavelength or wavelengths.

The radiation may contain multiple wavelengths. If the radiation is also monochromatic, then measurement calculations (reconstruction) may be simplified, but it is easier with HHG to produce radiation with several wavelengths. These are matters of design choice, and may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. One or more filtering devices (not shown) may be provided. For example a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the beam path may be contained within a vacuum environment, bearing in mind that EUV radiation is absorbed when traveling in air. The various components of radiation source 330 and illumination optics 332 can be adjustable to implement different metrology 'recipes' within the same apparatus. For example different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and so-called x-ray lasers. A source based on inverse Compton scattering could also be used. Plasma-based sources such as DPP and LPP sources also provide radiation in multiple wavebands, including EUV. Plasma sources for generating EUV radiation include sources based on tin (Sn), for example, but also Xe or Ar or Kr or Ne or N, or any combination of them.

From the first radiation source 330, the filtered beam 642 enters an inspection chamber where the substrate W including a structure of interest is held for inspection by substrate support 616. The structure of interest is labeled T. The atmosphere within inspection chamber 1050 is maintained near vacuum by vacuum pump 1052, so that EUV radiation can pass without undue attenuation through the atmosphere. The illumination system 332 includes elements 654 for focusing the radiation into a focused beam 656, and may comprise for example a two-dimensionally curved mirror, or a series of one-dimensionally curved mirrors, as described in the prior applications mentioned above. Diffraction gratings such as the spectroscopic gratings 312 and 318 can be combined with such mirrors, if desired. The focusing is performed to achieve a round or elliptical spot under 10 μm in diameter, when projected onto the structure of interest. Substrate support 616 comprises for example an X-Y translation stage and a rotation stage, by which any part of the substrate W can be brought to the focal point of beam to in a desired orientation. Thus the radiation spot S is formed on the structure of interest.

Also shown in FIG. 5 is the outline of a second metrology apparatus labelled MET2. This illustrates where the illustrated layout allows space for a second illumination system and second detection system to work on the same target structure within the metrology apparatus 240.

In the pending international patent application PCT/EP2016/056254, mentioned in the introduction, experimental results and simulations are presented to illustrate choices of wavelengths and choices of incidence angles that can be used in such an apparatus. Particularly in the wavelength range 15-40 nm and above 40 nm it is seen that the reflectance of several of the materials of interest remains substantial even up to angles of 10, 20 and 30 degrees. Referring again to FIGS. 4 and 5, this range of incidence angles allows an optical design to be implemented which achieves the desired small radiation spot, even at grazing incidence using available EUV optical technology. The pending international patent application further explains how, using a "conical mount" arrangement, improve accuracy can be obtained by varying the angle of incidence of illumination not only in the polar direction, but also in an azimuthal direction, relative to the direction of periodicity of the target T.

Figure 7:
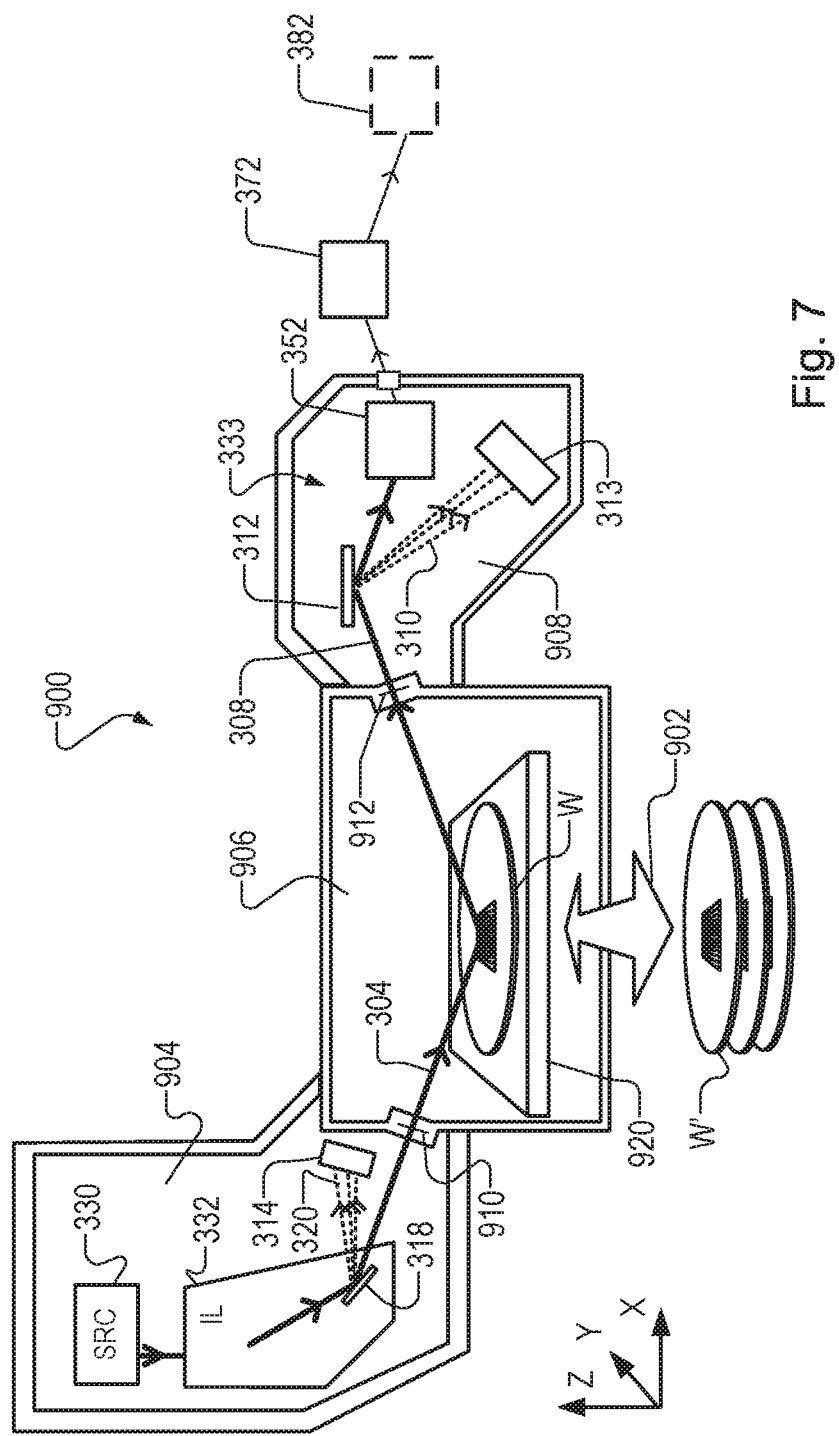
FIG. 7 illustrates the principle of housing components of the apparatus of FIGS. 3 and form partly in different vacuum or near-vacuum and/or low pressure environments.

FIG. 7 illustrates schematically the housing of different parts of a metrology apparatus 900, which may be the apparatus of FIGS. 3 and 4. This housing arrangement has features to facilitate management of vacuum and low pressure atmospheres within the apparatus, particularly in a high-volume manufacturing environment. As already explained with reference to FIG. 11, EUV radiation signals will be severely weakened, unless beam paths are contained within vacuum or low pressure environments. At the same time, if the apparatus is to be used in a high volume manufacturing environment, operations represented schematically at 902 will be performed frequently to exchange a substrate W currently within the apparatus with a new substrate W'.

In the example metrology apparatus 900, different parts of the EUV optical system are contained in different chambers 904, 906, 908. Suitable walls define these chambers, while windows 910 and 912 permit EUV radiation to pass between the chambers. Each window 910, 912 may comprise a physical membrane, or may comprise a simple aperture was differential pumping to maintain desired atmospheric conditions on either side of the window. The first chamber 904 contains the source 330 and illumination system 332. A first atmospheric condition, for example high vacuum, is maintained in chamber 904 by suitable pumping and control systems, not shown. First window 910 permits incident beam 304 to enter the second chamber 906, where the target is supported on a substrate support W. In the second chamber 906 a second atmospheric condition is maintained surrounding the target. The second atmospheric condition may be, for example, a low pressure gaseous atmosphere. In this way, when substrates W and W' are exchanged through some form of air lock mechanism, the required atmospheric condition can be established and re-established relatively quickly, and without undue cost. While transmission losses in the second atmospheric condition may be one order of magnitude greater than in high vacuum, for the limited distance of travel and the operational productivity, these losses can be tolerated.

In this example, components of first detection system 333 such as grating 312 and detector 313 are located in a third chamber 908, which is maintained at a third atmospheric condition. The third atmospheric condition may be for example a high vacuum. A second window 912 permits the reflected ray 308 to enter the detection system in chamber 908, carrying spectroscopic information about a target on the substrate.

It may be noted that, if the windows 910 and 912 are of limited extent, then the geometry of the apparatus 900 in this example greatly restricts the range of incidence angles a that may be employed. In the pending international patent application PCT/EP2016/056254, there is illustrated a variant of the FIG. 7 apparatus, in which this problem is addressed by an additional mirror component. Other approaches may also be considered, for example by providing a number of discrete windows appropriate to different incidence angles, and/or by housing at least some components of the detection system within the same chamber 906 as the sample, so that they may move without losing their line of sight through a window.

Providing space within a controlled atmospheric environment the cost and implication for the owner and builder and operator of the metrology apparatus. Accordingly, for each of the second, third and fourth detection systems 352, 372, 382, it may be decided whether the detection system should be located in a low pressure environment, or in a (cheaper) environment at normal atmospheric pressure or the like. In the example illustrated in FIG. 7, the second detection system 352, which may, for example, be arranged to obtain a spectrum of radiation in the vacuum UV waveband, is located inside the controlled environment of chamber 908. Conversely, third and fourth detection systems 372 and 382 are located outside the chamber 908. Thus, for example, the detection system may be arranged to obtain a spectrum of radiation in the near UV waveband, while fourth detection system 382 is arranged to obtain a spectrum of radiation in the visible waveband. In an alternative example, where, for example, there is only a second detection system for analyzing radiation in the UV and/or visible wavebands, second detection system 352 can be located outside chamber 908.

Figure 8:
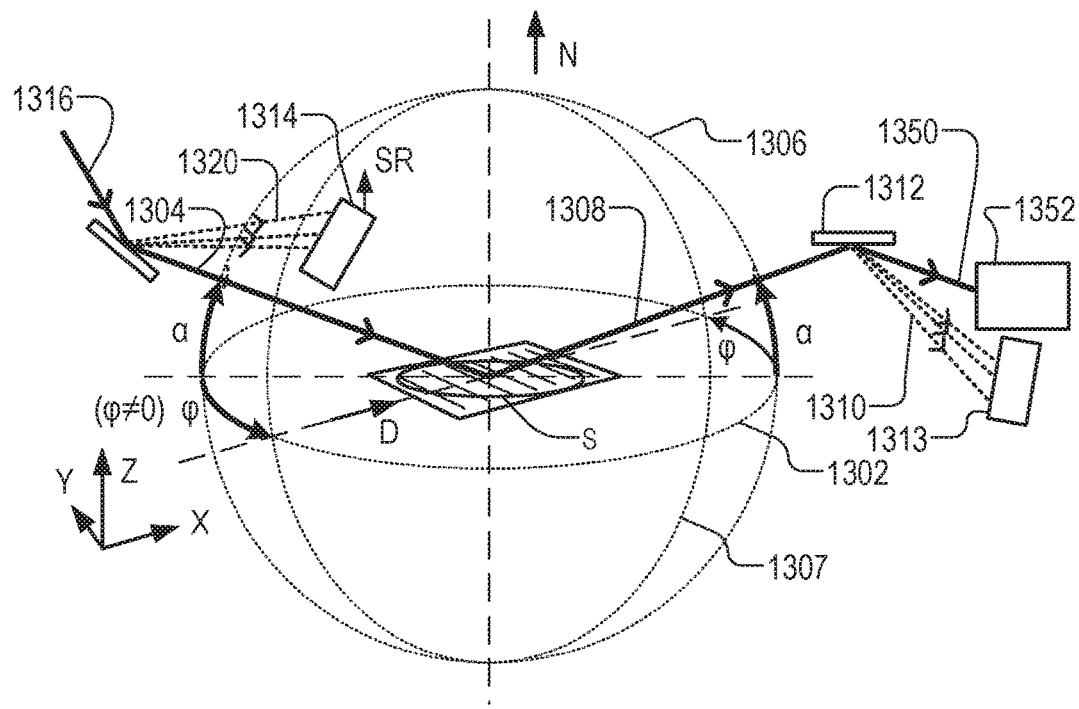
FIG. 8 illustrates the geometry of incident and reflected rays in relation to a grating target in a metrology method according to an embodiment of the present invention in which a non-zero azimuthal angle is used.
Figure 9:
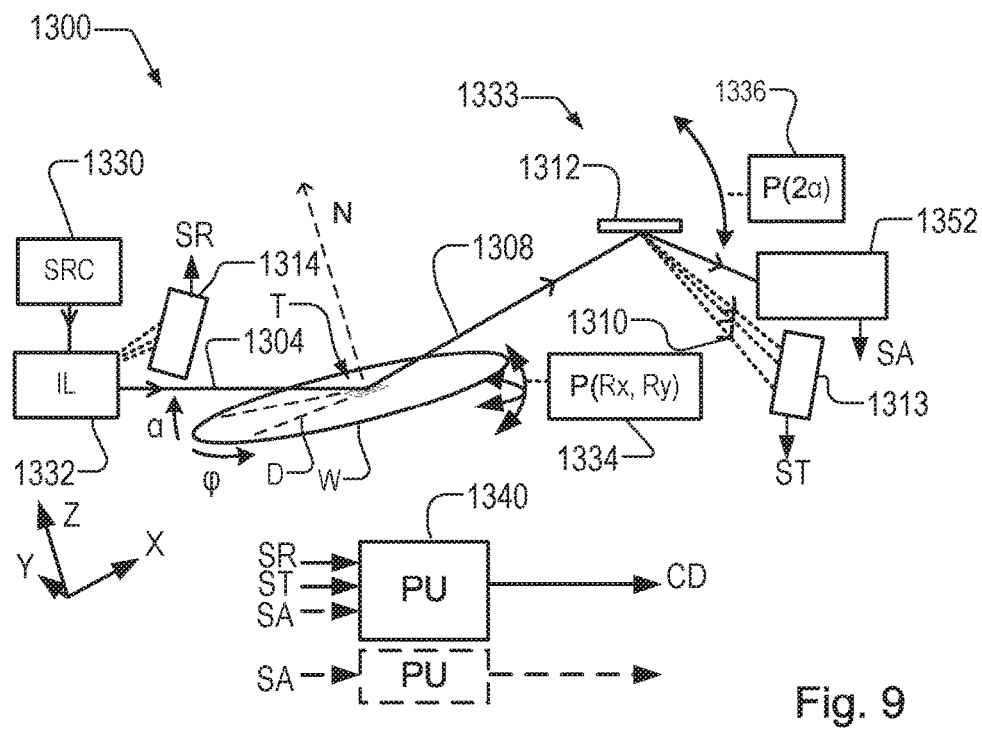
FIG. 9 illustrates schematically the components of a metrology apparatus, performing the method of FIG. 8.

FIG. 8 illustrates a modified metrology method and FIG. 9 illustrates a corresponding metrology apparatus 1300. Components labeled '13xx' in these examples should be considered to be the same as those labeled '3xx' in the FIG. 3 apparatus, unless mentioned otherwise. Thus the modified apparatus includes, for example, an illumination system 1330, illumination system 1332, first detection system 1333 and second detection system 1352. Compared with the apparatus of FIG. 2, however, positioning system 1334 is operable so that the angle of incidence of incident ray 1304 can be varied not only in a grazing incidence angle α, but also in an azimuthal angle, here labeled φ.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. However, a non-zero azimuthal angle of incidence φ is allowed. The azimuthal angle φ is defined relative to the direction of periodicity D of the grating target T. (In the case of a two-dimensionally periodic target, D may be either of the principal directions of periodicity.) That is to say, when the direction of incidence is projected onto the plane of the substrate, the azimuthal angle φ between the incident ray and the direction of periodicity D is non-zero, and may be very substantial. That is to say, the direction of irradiation lies outside a plane defined by the direction of periodicity D and the direction N normal to the substrate. Rather, the incident ray travels in a plane oblique to the direction of periodicity D. The oblique plane is represented by a circle 1307 that is orthogonal to the plane of the substrate but oblique to the direction of periodicity and the X-Z plane. It will be understood that, while the choice of labels of planes and axes is arbitrary, the grazing incidence angle and azimuthal angle are defined with reference to physical properties of the periodic structure of the target. The inventor has recognized that the diffraction efficiency of different diffraction orders can be increased substantially when non-zero azimuthal angles are used. This in turn has an impact on the spectrum of the reflected (zero order) ray 1308.

In implementing the apparatus 1300, different arrangements of positioning system can be used to achieve the non-zero azimuthal angle. Reference 1334 indicates a positioning subsystem with actuators for rotation about the X and Y axes of the substrate. For a desired combination of grazing incidence angle α and azimuthal angle φ, appropriate command values Rx and Ry are calculated to cause tilting of the substrate in two dimensions to achieve the desired angles. In another implementation, actuators may be provided for rotation and tilting, directly driving the angles α and φ. As will be appreciated from FIG. 8, rotation Rz corresponds directly to a desired azimuthal angle φ, and command values in this case can be generated more directly from the desired measurement angles.

In other areas of metrology, the type of mounting required to vary both the grazing incidence (polar) angle and the azimuthal angle is known as a "conical mount", and that term can be adopted in this EUV reflectometry apparatus also. In general, the skilled reader will appreciate that any form of command and any form of actuating mechanism can be used to implement this example, provided it is suitable to achieve a known non-zero azimuthal angle of incidence. It will also be understood that the relative orientation of the direction of incidence and the target is what matters (and of course the correct X-Y positioning of the target relative to the radiation spot S).

As mentioned above, the use of non-zero azimuthal angles may allow enhanced diffraction efficiency using the conical mount of FIGS. 8 and 9, compared with the FIGS. 2 and 3 arrangement. This may in turn provide stronger signals for measurement of particular properties, reducing measurement time and/or increasing measurement accuracy. Another benefit of using a non-zero azimuthal angle can be seen already in FIG. 8, by comparison with FIG. 2. Notice that the spot S, if it becomes elongated because of the oblique angle of incidence, is elongated in a direction defined by the azimuthal angle. Therefore the longest dimension of the spot is aligned with a diagonal direction of the target. Given that the majority of targets will be rectangular in shape, this diagonal elongation of the spot in fact allows a larger spot overall to be fitted within the target area. Consequently, for a given illumination intensity, a greater overall power of measurement radiation can be directed at the target and so the signal at detector will be proportionately increased. This effect alone may allow a slight shortening in measurement time. Alternatively, or in addition, focusing tolerance may be relaxed, which also shortens measurement time.

More information about the use of the conical mount in EUV metrology is given in the prior PCT application mentioned above. All of the explanations and variations discussed above with reference to FIGS. 2 to 7 can be applied in the method and apparatus of FIGS. 8 and 9. The method and apparatus of FIGS. 8 and 9 can be applied in any of the application examples mentioned below.

APPLICATION EXAMPLES

As mentioned previously, the additional signals SA, SA2, SA3 etc. which are obtained by the second, third etc. detection systems can be combined with the spectrum obtained by the first detection system 333, in a variety of ways. The prior European patent application 15202273.7 presents a variety of application examples, and all of these will not be repeated here. Instead, we present here a single example, in which the additional information is combined with the EUV spectrum in a reconstruction type of method.

FIG. 10 is a flowchart of a method of measuring parameters of a target structure, using for example the above metrology apparatus 240. As described above, the target structure may be on a substrate such as a semiconductor wafer. This target structure will often take the shape of a periodic series of lines in a grating, or structures in a 2-D array. The purpose of the metrology techniques is to measure one or more parameters of the shape by calculation from the observed interaction with radiation. In the reconstruction techniques disclosed herein, rigorous diffraction theories are used effectively to calculate what values of these parameters will result in a particular observed diffraction spectrum. In other words, target shape information is obtained for parameters such as CD (critical dimension) and overlay. Overlay metrology is a measuring technique in which the overlay of two targets is measured in order to determine whether two layers on a substrate are aligned or not. CD, or critical dimension, is the width of the object that is "written" on the substrate and is the limit at which a lithographic apparatus is physically able to write on a substrate. In some situations, the parameter of interest may be CD uniformity, rather than an absolute measurement of CD itself. Other parameters such as edge placement error (EPE), layer height (thickness) and side wall angle (SWA) may also be measured, if desired. Any parameter of the shape that has an influence on the spectrum can in principle be measured in this way. Parameters of interest may also include a parameter related to properties of the material within the structure, rather than the shape of the structure.

Using results from the metrology apparatus 240 in combination with modeling of a structure and its diffraction properties, measurement of the shape and other parameters of the structure can be performed in a number of ways. Referring to the example of FIG. 3 or 9, for example, signals may be obtained from the first, second etc. detection systems, representing the spectra of radiation reflected by the target T in different wavebands. In a first type of process, represented by FIG. 10, a spectrum based on a first estimate of the target shape (a first candidate structure) is calculated and compared with the observed spectrum. Parameters of the model are then varied systematically and the diffraction re-calculated in a series of iterations, to generate new candidate structures and so arrive at a best fit. In a second type of process, spectra for many different candidate structures are calculated in advance to create a "library" of spectra. Then the spectrum observed from the measurement target is compared with the library of calculated spectra to find a best fit. Both methods can be used together: a coarse fit can be obtained from a library, followed by an iterative process to find a best fit.

The terms "spectrum" and "spectra" in this context may refer to a frequency-resolved spectra in the spectroscopic scatterometer of FIGS. 2 and 3. The spectra obtained by the different detection systems in different wavebands may be treated equally as part of a larger spectrum observed or calculated, or they may be used individually in different parts of the calculation process. Thus, for example, a visible waveband spectrum and an EUV waveband spectrum may be used simultaneously to constrain all the floating parameters of the model, or the visible waveband spectrum may be used firstly to constrain certain parameters, which are then regarded as fixed when processing the EUV spectrum. In either case, the additional information available from the second, third etc. detection systems can improve accuracy of the result.

A third type of process omits the step of modelling the structure and its interaction with inspection radiation, and applies machine learning to correlate features of the observed spectra with parameters of the structure. Machine learning can be based on a training set of spectra observed from real structures, coupled with direct measurements of parameters of the structure that will be the unknown parameters in a future measurement. Machine learning can also be based on a training set of spectra obtained by modeling (simulation) of the interaction with mathematically modeled structures, as used in the "library" process described above. Training data based on simulation and training data based on real observations can be combined into a larger training set, as desired.

Returning to the first type of process, purely by way of example, the way the measurement of the target shape and/or material properties may be carried out using an angle-resolved scatterometer will be described in summary, with reference to FIG. 4. The following steps are performed. The steps will be listed here, and then explained in more detail:

S11: Receive Substrate with Target(s)
S12: Define Measurement Recipe
S13: Measure Spectra
S14: Define Model Recipe
S15: Estimate Shape Parameters
S16: Calculate Model Spectra
S17: Compare Measured v Calculated Patterns
S18: Calculate Merit Function
S19: Generate Revised Shape Parameters
S20: Report Final Shape Parameters At S11 a substrate W is received with one or more metrology target structures T upon it. The target structure will be assumed for this description to be periodic in only one direction (1-D structure). In a case where it is periodic in two directions (2-dimensional structure), or not completely periodic, the processing will be adapted accordingly. At S12 a measurement recipe is defined. The recipe may define any number of parameters of the illumination and detection settings to be used in a particular application. The recipe may specify one or more combinations of wavelength and polarization for the incident radiation. The recipe may define specific angular distribution for the illumination and detection. The recipe may specify intensity and exposure time of the incident radiation. For example also, phase or coherence of the source(s) could be part of the measurement recipe.

At S13 with a target structure positioned at the spot S, spectra of the structure on the substrate are measured using the apparatus of the general type illustrated in FIGS. 2 and 3 or 8 and 9. The measured spectra are captured by detector 313, 356 etc. and forwarded to a calculation system within a processor 340. To obtain a robust measurement through reconstruction, several spectra of the same target may be captured with different sub-recipes. The spectra captured in this way constitute observation data from which properties of the target structure can be determined, whether directly or indirectly.

Note that the observation data may be processed as detailed spectra, or they may be simplified into a set of parameters before being used in calculations. As a particular example, a spectrum may be reduced simply to a set of values identifying the wavelength and height of one or more peaks in the spectrum.

At S14 a 'model recipe' is established which defines a parameterized model of the target structure in terms of a number of parameters $p_i$ ($p_1$, $p_2$, $p_3$ and so on). These parameters may represent for example, in a 1-D periodic structure, the angle of a side wall, the height or depth of a feature, the width of the feature. Properties of the target material and underlying layers are also represented by parameters such as refractive index (at a particular wavelength present in the inspection radiation beam). Importantly, while a target structure may be defined by dozens of parameters describing its shape and material properties, the model recipe will define many of these to have fixed values, while others are to be variable or 'floating' parameters for the purpose of the following process steps. For the purposes of describing FIG. 4, only the variable parameters are considered as parameters $p_i$. Variable parameters will generally include the parameter of interest (the property to be measured), as well as so-called "nuisance" parameters. These are parameters that are correlated with the parameters of interest and may also influence the observed spectra. Automated methods of optimizing the selection of fixed and floating parameters are described in the prior art, for example in US20120123748.

Conventionally, it is assumed that the parameters of the structure model, even the variable parameters, do not vary over the course of an exposure with inspection radiation. On the other hand, in accordance with the principles of the present disclosure, this assumption may not be valid in all cases. Modifications of the method will be discussed further below, that take account of variation of the parameters in the course of the exposure. The conventional steps of the method will be described first of all.

At S15 a model target shape is estimated by setting initial values $p_i(0)$ for the floating parameters (i.e. $p_1(0)$, $p_2(0)$, $p_3(0)$ and so on). Each floating parameter may be generated with certain constraints, as defined in the recipe.

At S16, the parameters representing the estimated shape, together with the properties of the different materials in the model, are used to calculate the scattering properties, for example using a rigorous optical diffraction method or other solver of Maxwell equations, described in the prior art. This gives an estimated or model spectrum of the estimated target shape, for a given combination of wavelength, polarization, angular distribution and so forth.

At S17 and S18 the measured spectra and the model spectra are then compared and their similarities and differences are used to calculate a "merit function" for the model target shape.

Assuming that the merit function indicates that the model needs to be improved before it represents accurately the actual target shape, control passes to step S19 where new parameters $p_1(1)$, $p_2(1)$, $p_3(1)$, etc. are estimated and fed back iteratively into step S16. Steps S16 to S18 are repeated. In order to assist the search, the calculations in step S16 further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

When the merit function indicates that this iterative process has converged on a solution with a desired accuracy, control passes to step S20 and the currently estimated parameters (for example a CD value) are reported as the measurement of the actual target structure.

Once the value for one target has been calculated, a new target on the same substrate or a similar substrate may be measured using the same steps S13 etc., without changing the measurement recipe. Where a different type of substrate or target is to be measured, or in any case where it is desired to change the measurement recipe, control passes to step S11 or S12 instead.

Figure 11:
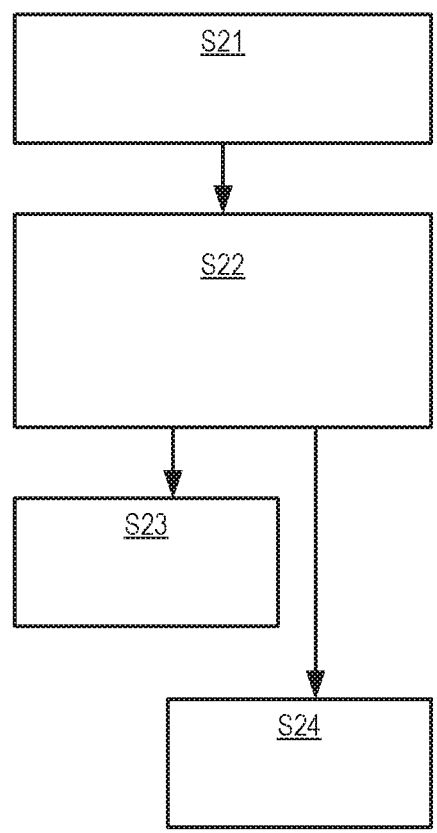
FIG. 11 is a flow chart illustrating a method of controlling performance of a metrology method and/or of a lithographic manufacturing process using measurements made by the methods and apparatuses of FIGS. 1 to 10.

FIG. 11 illustrates the application of a measurement method (for example any of the methods of FIGS. 2 to 10) in the management of a lithographic manufacturing system. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the metrology apparatus 240 which first, second etc. detection systems is used to measure a property of the structures across the substrate. At step S23, optionally, metrology recipes and calibrations of the EUV metrology apparatus 244 and/or other metrology apparatus 240 are updated in light of the measurement results obtained. For example, where the EUV metrology apparatus 244 has a lower throughput than the optical metrology apparatus 240, a few accurate measurements using EUV radiation can be used to improve the calculation of measurements made using the optical metrology apparatus, for a specific substrate design and process.

At step S24, measurements of CD or other parameters are compared with desired values, and used to update settings of the lithographic apparatus and/or other apparatus within the lithographic manufacturing system. By providing an EUV metrology apparatus as part of a metrology system, throughput and/or accuracy can be improved and the performance of the whole lithographic production facility can be improved. Product features and/or product-like features can be measured directly, even at the smallest technology nodes, and in-die targets can be provided and measured without losing too much area.

In the above steps, it is assumed that sufficient targets are measured across a substrate and across multiple substrates, that statistically reliable models of the process are derivable. The profile of CD and other parameters does not need to be expressed entirely as a variation across the substrate. It can be expressed for example as an intra-field profile that is common to all fields (each instance of patterning using the patterning device M at a different location on the substrate W) and a lower order, inter-field, variation onto which the intra-field variation is repeatedly superimposed. The settings of the lithographic process adjusted in step S24 can include intra-field settings as well as inter-field settings. They may be applicable to all operations of the apparatus, or specific to a particular product layer.

CONCLUSION

The techniques disclosed herein allow increased information to be obtained about a structure of interest, without necessarily incurring separate measurement steps and separate illumination systems. In particular, spectra or other information relating to a second waveband can be obtained simultaneously, or sequentially, using "leftover" radiation from a first detection system operating in a first waveband.

While specific examples of methods and apparatus have been described above, it will be appreciated that the invention may be practiced otherwise than as described. The design of the metrology apparatus and is free to choose the different wavebands and the number and arrangement of detection systems to achieve desired functionality within constraints of space and cost. The methods by which measurements of a structure's shape and materials are calculated from the detected signals can also be freely chosen from a wide variety of available techniques, whether presently known in the art or devised in future.

The term "lens", where the context allows, may refer to any one or combination of various types of optical components, including refractive, reflective, magnetic, electromagnetic and electrostatic optical components.

Further embodiments according to the invention are described in below numbered clauses:

1. A metrology apparatus for measuring a property of a structure, the metrology apparatus comprising:
   an illumination system for irradiating the structure with radiation;
   a first detection system comprising a first spectroscopic grating and a first detector, the first spectroscopic grating being arranged to receive said radiation after interaction with the structure, the first detector being arranged to detect a spectrum in a first waveband by receiving one or more higher orders of radiation diffracted by said first spectroscopic grating;
   a second detection system arranged to receive at least a portion of zero order radiation reflected by the first spectroscopic grating and to analyze said zero order radiation in one or more other wavebands.

2. A metrology apparatus according to clause 1 wherein said second detection system includes a second spectroscopic grating and a second detector, the second spectroscopic grating being arranged to receive said zero order radiation from the first spectroscopic grating, the second detector being arranged to detect a spectrum in a second waveband by receiving one or more higher orders of radiation diffracted by said second spectroscopic grating.

3. A metrology system according to clause 1 or 2 wherein said second detection system includes a polarization analyzer, the second detector being arranged to receive radiation in the second waveband selected by polarization.

4. A metrology apparatus eaccording to any preceding clause wherein the first waveband comprises wavelengths in the range 1 nm to 100 nm and the second waveband comprises wavelengths longer than 100 nm.

5. A metrology apparatus according to clause 4 wherein the second waveband comprises wavelengths longer than 300 nm.

6. A metrology apparatus according to clause 4 wherein the second waveband comprises wavelengths shorter than 300 nm.

7. A metrology apparatus according to any preceding clause wherein in operation the first detection system is housed in a low pressure environment and the second detection system is housed in an environment substantially at atmospheric pressure.

8. A metrology apparatus according to any preceding clause wherein the second detection system is further arranged to direct at least a portion of said zero order radiation in one or more wavebands other than the first and second wavebands to a third detection system, said third detection system being arranged for analyzing radiation in a third waveband.

9. A metrology apparatus according to clause 8 wherein the second detection system includes a second spectroscopic grating and wherein the portion of radiation directed to the third detection system comprises at least part of zero order radiation reflected by the second spectroscopic grating.

10. A metrology apparatus according to clause 8 or 9 wherein said third detection system includes a third spectroscopic grating and a third detector, the third detector being arranged to detect a spectrum in a third waveband by receiving one or more higher orders of radiation diffracted by said third spectroscopic grating.

11. A metrology system according to clause 8, 9 or 10 wherein said third detection system includes a polarization analyzer, the third detector being arranged to receive radiation in the third waveband selected by polarization.

12. A metrology apparatus according to any of clauses 8 to 11 wherein the first waveband comprises wavelengths in the range 1 nm to 100 nm and the second waveband comprises wavelengths longer than 100 nm.

13. A metrology apparatus according to clause 12 wherein the third waveband comprises wavelengths longer than 300 nm.

14. A metrology apparatus according to clause 12 or 13 wherein the second waveband comprises wavelengths shorter than 300 nm.

15. A metrology apparatus according to any of clauses 8 to 14 wherein in operation at least the first detection system is housed in a low pressure environment and the third detection system is housed substantially at atmospheric pressure.

16. A metrology apparatus according to any preceding clause further comprising a processing system for using first analysis data received from the first detection system to determine a property of the structure.

17. A metrology apparatus according to clause 16 wherein said processing system is further arranged to use second analysis data received from the second detection system in combination with the first analysis data to determine said property.

18. A metrology apparatus according to clause 16 wherein said processing system is further arranged to use third analysis data received from the third detection system in combination with the first or second analysis data to determine said property.

19. A metrology apparatus according to any of clauses 8 to 15 further comprising a processing system determining a property of the structure using two or more of: first analysis data received from the first detection system, second analysis data received from the second detection system, and third analysis data received from the third detection system.

20. A metrology apparatus according to any preceding clause further including a radiation source for providing radiation to said illumination system in said first and second wavebands.

21. A metrology apparatus according to clause 20 wherein said radiation source is a broadband radiation source operable to generate radiation in said first and second wavebands simultaneously.

22. A metrology apparatus according to clause 20 or 21 wherein said radiation source is operable to generate radiation in wavebands ranging from less than 100 nm to more than 400 nm.

23. A metrology apparatus according to clause 22 wherein said radiation source is operable to generate radiation in wavebands ranging from less than 10 nm to more than 400 nm.

24. A metrology apparatus according to any preceding clause wherein said first radiation source is a higher harmonic generator source.

25. A method of measuring a property of a structure manufactured by a lithographic process, the method comprising the steps:

(a) irradiating the structure with radiation including radiation in a first waveband and radiation in a second waveband;
(b) directing at least a portion of said radiation after interaction with the structure to a first spectroscopic grating;
(c) detecting a spectrum in a first waveband using one or more higher orders of radiation diffracted by said first spectroscopic grating;
(d) analyzing at least a portion of zero order radiation reflected by the first spectroscopic grating in the second waveband.

26. A method according to clause 25 wherein the step (d) comprises:
(d1) directing at least a portion of said zero order radiation after interaction with the structure to a second spectroscopic grating; and
(d2) detecting a spectrum in the second waveband using one or more higher orders of radiation diffracted by said second spectroscopic grating.

27. A method according to clause 26 wherein the radiation in step (a) includes radiation in a third waveband, the method further comprising a step:
(e) analyzing at least a portion of zero order radiation reflected by the second spectroscopic grating in the third waveband.

28. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the step of measuring the properties of the structure includes measuring a property using the metrology apparatus according to any of clauses 1 to 24.

29. A device manufacturing method according to clause 28 wherein said functional device pattern defines product features having a critical dimension less than 50 nm, optionally less than 20 nm.

30. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the step of measuring the properties of the structure includes measuring a property using the method according to any of clauses 25 to 27.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A metrology apparatus comprising:
an illumination system configured to irradiate a structure with radiation;
a first detection system comprising a first spectroscopic grating and a first detector, the first spectroscopic grating being arranged to receive the radiation after interaction with the structure, and the first detector being arranged to detect a spectrum in a first waveband by receiving one or more higher orders of radiation diffracted by the first spectroscopic grating; and
a second detection system comprising a second spectroscopic grating and a second detector, the second spectroscopic grating arranged to receive at least a portion of zero order radiation reflected by the first spectroscopic grating, and the second detector being arranged to detect a spectrum in a second waveband by receiving one or more higher orders of radiation diffracted by the second spectroscopic grating.

2. The metrology system of claim 1, wherein the second detection system comprises a polarization analyzer, the second detector being arranged to receive radiation in the second waveband selected by polarization.

3. The metrology apparatus of claim 1, wherein the first waveband comprises wavelengths in the range 1 nm to 100 nm and the second waveband comprises wavelengths longer than 100 nm.

4. The metrology apparatus of claim 1, wherein the second waveband comprises wavelengths longer than 300 nm.

5. The metrology apparatus of claim 1, wherein the second waveband comprises wavelengths shorter than 300 nm.

6. The metrology apparatus of claim 1, wherein, in operation, the first detection system is housed in a low pressure environment and the second detection system is housed in an environment substantially at atmospheric pressure.

7. The metrology apparatus of claim 1, wherein the second detection system is further arranged to direct at least a portion of the zero order radiation in one or more wavebands other than the first and second wavebands to a third detection system, the third detection system being arranged for analyzing radiation in a third waveband.

8. The metrology apparatus of claim 7, wherein the portion of zero order radiation directed to the third detection system comprises at least part of zero order radiation reflected by the second spectroscopic grating.

9. The metrology apparatus of claim 7, wherein the third detection system comprises a third spectroscopic grating and a third detector, the third detector being arranged to detect a spectrum in a third waveband by receiving one or more higher orders of radiation diffracted by the third spectroscopic grating.

10. The metrology system of claim 7, wherein the third detection system comprises a polarization analyzer, the third detector being arranged to receive radiation in the third waveband selected by polarization.

11. The metrology apparatus of claim 7, wherein the first waveband comprises wavelengths in the range 1 nm to 100 nm and the second waveband comprises wavelengths longer than 100 nm.

12. The metrology apparatus of claim 7, wherein the third waveband comprises wavelengths longer than 300 nm.

13. The metrology apparatus of claim 7, wherein the second waveband comprises wavelengths shorter than 300 nm.

14. The metrology apparatus of claim 7, wherein, in operation, at least the first detection system is housed in a low pressure environment and the third detection system is housed substantially at atmospheric pressure.

15. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the measuring comprises measuring a property using the metrology apparatus of claim 1.

16. A method comprising:
irradiating a structure with radiation including radiation in a first waveband and radiation in a second waveband;
directing at least a portion of the radiation after interaction with the structure to a first spectroscopic grating;
detecting a spectrum in a first waveband using one or more higher orders of radiation diffracted by the first spectroscopic grating;
directing at least a portion of zero order radiation after interaction with the structure to a second spectroscopic grating; and
detecting a spectrum in the second waveband using one or more higher orders of radiation diffracted by the second spectroscopic grating.

17. The method according to claim 16, wherein the radiation in the irradiating includes radiation in a third waveband, the method further comprising:
analyzing at least a portion of zero order radiation reflected by the second spectroscopic grating in the third waveband.

18. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the measuring comprises measuring a property using the method comprising:
irradiating a structure with radiation including radiation in a first waveband and radiation in a second waveband;
directing at least a portion of the radiation after interaction with the structure to a first spectroscopic grating;
detecting a spectrum in a first waveband using one or more higher orders of radiation diffracted by the first spectroscopic grating; and
directing at least a portion of zero order radiation after interaction with the structure to a second spectroscopic grating; and
detecting a spectrum in the second waveband using one or more higher orders of radiation diffracted by the second spectroscopic grating.

* * * * *